United States Patent [19]

Ehrat

[11] 4,237,065

[45] Dec. 2, 1980

[54] PROCESS FOR THE PREPARATION OF N-PHOSPHONOMETHYL GLYCINE

[75] Inventor: Rodolphe Ehrat, Dinhard, Switzerland

[73] Assignee: Biological Chemical Activities Patents SA B.C.A.P., Luxembourg, Luxembourg

[21] Appl. No.: 84,532

[22] Filed: Oct. 15, 1979

[30] Foreign Application Priority Data

Oct. 27, 1978 [CH] Switzerland ............... 11133/78

[51] Int. Cl.$^3$ .................................. C07F 9/38
[52] U.S. Cl. ........................ 260/502.5; 260/501.1
[58] Field of Search ................... 260/502.5, 944

[56] References Cited

U.S. PATENT DOCUMENTS

| | | | |
|---|---|---|---|
| 2,635,112 | 4/1953 | Fields | 260/944 |
| 2,847,442 | 8/1958 | Sallmann | 260/502.5 |
| 3,288,846 | 11/1966 | Irani et al. | 260/502.5 |
| 3,549,728 | 12/1970 | Balde et al. | 260/502.5 |
| 3,956,370 | 5/1976 | Parry et al. | 260/502.5 |

FOREIGN PATENT DOCUMENTS

2741504 3/1979 Fed. Rep. of Germany ........ 260/502.5

OTHER PUBLICATIONS

Fields, "J.A.C.S.", vol. 74 (1952), pp. 1528-1531.

*Primary Examiner*—Joseph E. Evans
*Attorney, Agent, or Firm*—O'Brien & Marks

[57] ABSTRACT

N-phosphonomethyl glycine is prepared starting from glycine, formaldehyde and a tertiary base in alcoholic solution. After completion of the reaction, a dialkyl phosphite is added. The reaction product is hydrolyzed, and acidification yields the desired product in good purity.

10 Claims, No Drawings

PROCESS FOR THE PREPARATION OF N-PHOSPHONOMETHYL GLYCINE

BACKGROUND OF THE INVENTION

The present invention relates to a new and useful process for the preparation N-phosphonomethyl glycine (PMG).

It is known that N-phosphonomethyl glycine is a very useful intermediate for the preparation of herbicidal agents and compositions having outstanding properties, and it is also known that this compound can presently only be prepared by very difficult and complex methods being very complicated to be put into practice.

There is therefore a great need of new and useful processes permitting to obtain the N-phosphonomethyl glycine without having the disadvantages and the limits of the method presently and conventionnally employed.

Therefore, the present invention has for one of its primary objectives a new and useful process for the preparation of PMG. Another object of the invention is to provide such a process which would be simple and of a short duration of the reaction and which would permit the direct use of the compound so obtained without need of purification. Another object of the invention is to provide a process wherein starting materials of low cost may be employed and which can easily be found on the market.

SUMMARY OF THE INVENTION

These objects and still others are accomplished by the process of the invention which is principally characterized by the fact that glycine is dissolved in an alcoholic solution of formaldehyde and a tertiary base; to the thus obtained solution a dialkyl phosphite is added, and after the completion of the reaction the mixture is submitted to an alkaline hydrolysis, and finally the precipitation of N-phosphonomethyl glycine is obtained by an acidification step.

In practice, the process is conducted by the following stages:

Paraformaldehyde is dissolved in the heat in an alcohol with the simultaneous depolymerization in the presence of a catalytic amount of the tertiary base. To the obtained solution, glycine is added and at the same time a greater quantity of the tertiary base. After complete solution, a dialkyl phosphite is added to the reaction mixture and the reaction is accomplished in the heat. The so formed ester is then saponified by means of an aqueous solution of NaOH, and said tertiary base is removed. Finally, the thus obtained alkaline solution is acidified which precipitates the formed N-phosphonomethyl glycine.

It results from the foregoing that basically, one reacts glycine, formaldehyde and dialkyl phosphite under particular conditions, defining a particular easy reaction, and there is the possibility to use the byproducts of the process.

Said particular conditions are such that the glycine which is an amino acid can be considered during reaction simply as an amine soluble in an alcohol or in water. The glycine therefore reacts in a quite surprising manner like an amine in a Mannich reaction wherein formaldehyde, amines and dialkyl phosphites can be used to give phosphonomethyl amines. This is to say that under the particular conditions of the invention, the Mannich reaction gives not an amine but N-phosphonomethyl glycine.

In order to make more precise the context of this invention, it can be said that the process provides as a particularly important step the solubilization of the glycine in an alcoholic solution of formaldehyde and a tertiary amine, and the following equilibrium reactions occur:

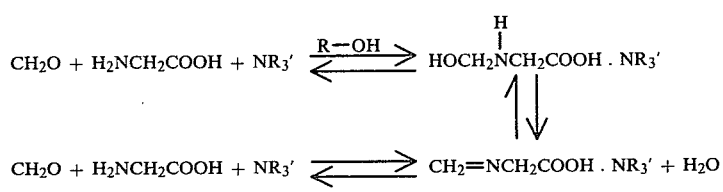

There is therefore an immediate formation of two products, N-methyl glycine or N-methylene glycine or a mixture of these two products, which react in a further step with the dialkyl phosphite.

In order to obtain the complete solubilization of the glycine in the alcohol, there must be observed minimum molar ratios between the formaldehyde and the tertiary base; if one of these two conditions is fully or partially absent, there will be no solubilization or even a precipitation of the glycine.

In practice, one may begin with dissolving paraformaldehyde or trioxymethylene with heating is an alcohol, and a depolymerization of the paraformaldehyde takes place in the presence of tertiary base. After this reaction step, glycine and the remaining tertiary base are added to the reaction mixture. When the solution has been formed, the dialkyl phosphite is added. The mixture is reacted in the heat, and afterwards the ester which has been formed is saponified by means of an aqueous sodiumhydroxide solution, and the alcohol or the tertiary base or both are then removed from the mixture.

The alkaline solution which remains is then acidified in order to precipitate N-phosphonomethyl glycine.

The alkaline hydrolysis step can be foregone to; namely, the ester can also be saponified in an acidic medium.

The complete reaction scheme is the following:

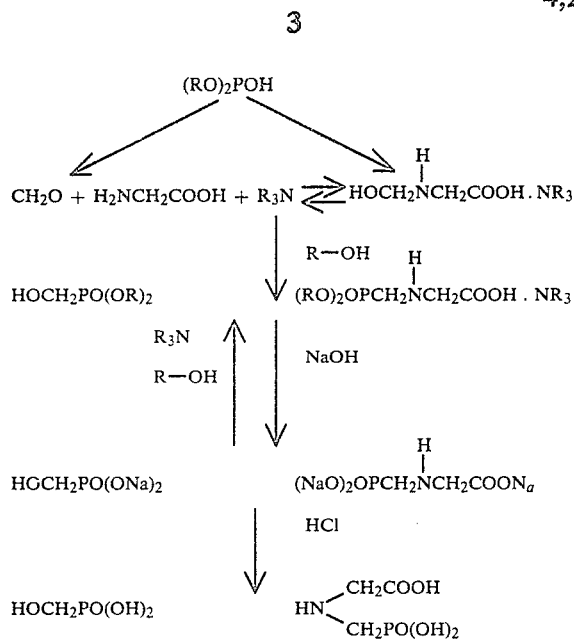

Regarding the byproducts, it should be noted that there is no formation of any secondary derivative of glycine like N-diphosphonomethyl glycine, but only of hydroxymethyl phosphonic acid which can be reclaimed in the form of its calcium salt.

The order in which the reactives are added before the saponification is not critical; it is possible to add the formaldehyde solution or directly add solid paraformaldehyde to the mixture of the other reagents, namely glycine, dialkyl phosphite and tertiary base. One can also blend simultaneously all the reagents which may be solid or liquid and heat the mixture afterwards. The results of the process do not change in substance, there being only slight variations in the yields.

It is however preferred to follow the order of addition already mentioned, i.e. starting with the alcohol and adding paraformaldehyde, a little amount of the tertiary base, glycine and the remainder of the base; or alcohol, paraformaldehyde, glycine and finally the tertiary base are blended simultaneously.

The phosphite may be added to this solution or vice versa. The selection of the alcohol as a solvent can be made in a wide range, but alcohols are preferred having only few carbon atoms and particularly, methanol.

The use of water as a solvent still allows to check the validity of the reaction; on the other hand, only low yields are obtained by the use of water since the phosphonate is not stable in aqueous medium.

The formaldehyde is preferred to be used as an anhydrous polymer and not in the form of an aqueous solution, and this for the reasons which have been just explained.

The selection of the teriary base can also be made amongst a large variety: aliphatic, aromatic and heterocyclic tertiary base can perfectly be used. However, for reasons of commodity during use (boiling point, facilities of reclaiming, price) the use of triethylamine is largely preferred.

When methanol is selected as a solvent and triethylamine as a base, it has been found as an important aspect of the invention that the recuperation and the recycling of these two components is surprisingly facilitated. When the aqueous alkaline saponification solution is distilled with a vapour temperature not above 70° C., it is possible to reclaim completely all the amine in the form of a methanolic solution having a water content lower than 1.1%. This amine solution is perfectly and immediately ready for reuse without any further distillation or rectification (which however could be effected). Regarding the phosphonic ester, analogous matter as that of the alcohols applies, i.e. one can use any ester whatsoever of alcohols having a low molecular weight; however, all the diesters of phosphorous acid can be perfectly used.

In all cases, the alkyl esters are in principle preferred, and in particular the methyl and the ethyl diester.

Some details should now be discussed regarding the molar ratios to be chosen between the different reagents in order to optimize the process, and these indications which follow are based on experiments carried out by the applicant.

Generally, the molar ratio $Et_3N$ to glycine should not be inferior to 1. The ratio $CH_2O$: glycine can be selected between 1 and 2, sometimes even more, but it should preferably be 1.3 to 1.6. The ratio of phosphite to glycine can be selected in a very wide range, i.e. from 0.4 to 2 and more, preferably between 0.6 and 1.6 depending on the desire to direct the reaction to a better yield of the one or the other of the said reagents. The amount of solvent, preferably of methyl alcohol, can be selected from 150 to 500 ml or more per mol of glycine. The quantity of NaOH necessary to hydrolyze the phosphonic ester amounts to about 3 to 4 mols for each mol of phosphite used; the amount of HCl necessary for the precipitation of the N-phosphonomethyl glycine should roughly correspond to the molar amount of NaOH used. In all cases the acidification should be carried out to give a pH in the range between 1 and 1.9.

The reaction times and reaction temperatures are also of great importance in the process of the invention.

In the presence of small amounts triethylamine, paraformaldehyde dissolves in methanol already at 45° to 50° C. At reflux conditions, one obtains a complete solution in 5 to 10 minutes.

Under the combined action of $NEt_3$ and $CH_2O$, the glycine dissolves in methyl alcohol at room temperature in 1 to 1.5 hours, and this time greatly depends on the particles size of the glycine. At 60° to 70° C., the solution will be complete in 15 to 20 minutes. The reaction of dissolution of the glycine is exothermic.

As it has already been mentioned the solution may also be obtained in blending all the components simultaneously. The addition of the phosphite can be made over a period of 5 to 120 minutes. The temperature can be room temperature to reflux temperature, which is in the case of methanol as a solvent, 70° to 75° C.

In all cases, a reaction temperature between about 65° and 70° C. is preferred corresponding to the reaction time of 30 to 120 minutes, preferably 60 minutes. The reaction is slightly exothermic.

The addition of the NaOH solution to the reaction mixture or vice versa results in a strong exothermic effect but can easily be held under control.

The time necessary to hydrolyze the phosphonic ester in the selected alcoholic alkaline medium is about 1 to 2 hours. After this time, the mixture of alcohol and triethylamine is removed in about 1 to 2 hours. However, the mixture of alcohol and amine can be removed beginning with the heating. The final temperature can rise in the liquid face to 100° to 120° C., preferably 100° to 105° C.

The precipitation of N-phosphonomethyl glycine by crystallization at pH in the range between 1 and 2 and at a temperature between 10° and 20° C. occurs in 3 to 4 hours.

EXAMPLES

The examples which will be given now are construed to better explain the characteristics and advantages of the invention in all the details; the examples are given for illustration purposes only and should not limit the invention which is confined by the claims only.

EXAMPLE 1

In a reaction vessel equipped with an agitator, a thermometer, a reflux condenser and a dropping funnel are given 400 ml of methanol, 45 g (1.5 mols) of paraformaldehyde and 5 to 10 ml of triethylamine. The vessel is heated to reflux of the reaction mixture for 5 to 10 minutes until complete solution.

To the reaction mixture are added 75 g (1 mol) of glycine and, during agitation, 102 g (140 ml, 1 mol) triethylamine is introduced through the dropping funnel. The temperature is maintained for 30 to 60 minutes at about 60° to 70° C., and when solution is complete, 91 g (85 ml, 0.66 mols) of the ethyl phosphite is dropwise added within 5 to 10 minutes. The reaction mixture is stirred for about 1 to 1.5 hours at about 65° to 72° C.

During cooling, 250 g of NaOH (2.5 mols) are added in the form of 40% aqueous solution, and the reaction mixture is than refluxed for another 1.5 hours. After this time, the distillation of the mixture of methanol and triethylamine is started, and the latter is fully reclaimed. The liquid face temperature is about 100° to 110° C. after about 1 to 2 hours.

The mixture is cooled and then acidified to a pH of 1.5 by means of concentrated hydrochloric acid. The N-phosphonomethyl glycine begins to precipitate slowly, and after 3 to 4 hours at 15° C., the mixture is filtered, washed with water and dried to give 98% pure white to yellowish crystals having a weight of 65 to 71 g.

The yield calculated on the base of glycine is about 38 to 42%. The yield calculated on the base of diethyl phosphite is about 57.5 to 63.5%.

EXAMPLE 2

In the reaction vessel of Example 1, 500 ml of methanol, 45 g (1.5. mols) of paraformaldehyde, and 75 g (1 mol) of glycine are charged. At 42° to 55° C., 102 g (140 ml, 1 mol) of triethylamine are dropped into this mixture. The whole mixture is now maintained for 30 to 60 minutes at 60° to 70° C., and when the solution is complete, 138 g (129 ml, 1 mol) of diethyl phosphite are slowly dropped in during 30 minutes. After 1 to 1.5 hours at 65° to 70° C., the dropping in of a 30% NaOH solution is started (140 g of NaOH, 3.5 mols). The mixture is now heated to reflux, and the mixture of methanol and triethylamine which distills over is collected.

After about 3 hours, the liquid temperature in the vessel is 105° C.

The mixture is now cooled and acidified to a pH of 1.5. With a yield of 48 to 52%, calculated on the base of glycine or diethyl phosphite, 81 to 88 g of N-phosphonomethyl glycine are obtained.

EXAMPLE 3

The process of Example 2 is repeated with the exception that the amount of diethyl phosphite is 1.5 mols (207 g, 194 ml) and, consequently, that of NaOH is 200 g (5 mols) in the form of a 30% solution.

98 to 107 g of N-phosphonomethyl glycine are obtained.

The yield, based on diethyl phosphite, is 38.6 to 42%. The yield based on glycine, amounts to 58 to 63%.

The Examples 1, 2, 3 were repeated using dimethyl phosphite instead of diethyl phosphite. Substantially the same results have been obtained.

What we claim is:

1. A process for the preparation of N-phosphonomethyl glycine, wherein glycine is dissolved in an alcoholic solution of formaldehyde and a tertiary base, to the so obtained completed solution a dialkyl phosphite is added, the reaction mixture is subjected to an alkaline hydrolysis followed by an acidification whereupon the desired N-phosphonomethyl glycine is obtained by precipitation.

2. The process of claim 1 comprising the following steps: Dissolving formaldehyde in an alcohol with heating and adding a small quantity of a tertiary base to effect the depolymerization of the paraformaldehyde; adding glycine and a greater amount of said tertiary base; adding after completion of the solution, a dialkyl phosphite; reacting the mixture in the heat and saponifying the formed ester by means of an aqueous NaOH solution while removing said alcohol and said tertiary base; and acidifying the obtained alkaline solution in order to precipitate said N-phosphonomethyl glycine.

3. The process of claim 1 or 2 wherein said alcohol is methanol, said formaldehyde is trioxymethylene or paraformaldehyde, and said tertiary base is triethylamine.

4. The process of claim 1 or 2, wherein the acidification of the final alkaline solution is effected to a pH of less than 2.

5. The process of claim 3 wherein a solution of triethylamine in methanol is obtained by the recuperation and the recycling of a distillate at a temperature of not more than 70° C. of said aqueous alkaline saponification solution of the process.

6. The process of claim 1 or 2, wherein the molar ratio of triethylamine to glycine is not less than 1, the ratio of formaldehyde; to glycine is comprised in the range between 1 and 2 and the ratio of said phosphite to said glycine is comprised in the range between 0.4 and 2, the amount of solvent is between 150 and 500 ml per mol of glycine, the amount of NaOH to hydrolyze the ester is comprised between 3 and 4 mols per mol of said phosphite used and the amount of acid necessary to effect the acidification of the saponified solution corresponds to the molar amount of said NaOH.

7. The process of claim 1 or 2 wherein hydroxymethylphosphonic acid is reclaimed as a secondary reaction product.

8. The process of claim 7 wherein the reclaiming of said hydroxymethylphosphonic acid is carried out in the form of an insoluble salt before or after the separation of said N-phosphonomethyl glycine.

9. The process of claim 6 wherein the ratio of formaldehyde to glycine is between 1.3 and 1.6, the ratio of phosphite to glycine is between 0.6 and 1.6 and the solvent is methanol.

10. The process of claim 8 wherein the insoluble salt is calcium salt.

* * * * *